United States Patent
Ohta et al.

(10) Patent No.: US 12,109,108 B2
(45) Date of Patent: Oct. 8, 2024

(54) INTRAOCULAR LENS

(71) Applicant: NIDEK CO., LTD., Gamagori (JP)

(72) Inventors: Hiroshi Ohta, Gamagori (JP); Tomoya Monobe, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 112 days.

(21) Appl. No.: 17/857,578

(22) Filed: Jul. 5, 2022

(65) Prior Publication Data
US 2023/0000618 A1    Jan. 5, 2023

(30) Foreign Application Priority Data

Jul. 5, 2021   (JP) .................................. 2021-111586
Jul. 5, 2021   (JP) .................................. 2021-111587
Mar. 8, 2022   (JP) .................................. 2022-034885
Mar. 8, 2022   (JP) .................................. 2022-034886

(51) Int. Cl.
*A61F 2/16*          (2006.01)

(52) U.S. Cl.
CPC ............ *A61F 2/1618* (2013.01); *A61F 2/164* (2015.04)

(58) Field of Classification Search
CPC ................... A61F 2/1618; A61F 2/164; A61F 2250/0053; A61F 2250/0091
See application file for complete search history.

(56) References Cited

U.S. PATENT DOCUMENTS

| | | | | |
|---|---|---|---|---|
| 5,864,378 A * | 1/1999 | Portney | ................... | G02C 7/02 351/159.02 |
| 6,260,966 B1 * | 7/2001 | Sawano | ................ | G02C 7/042 351/159.43 |
| 2010/0016965 A1 * | 1/2010 | Hong | .................... | A61F 2/1648 623/6.37 |
| 2010/0097569 A1 * | 4/2010 | Weeber | ................... | G02C 7/06 623/6.3 |
| 2015/0182329 A1 * | 7/2015 | Bogaert | ............... | A61F 2/1637 623/6.27 |
| 2022/0287826 A1 * | 9/2022 | Tiwari | ................... | G02C 7/028 |

FOREIGN PATENT DOCUMENTS

JP    2004-121433 A    4/2004

* cited by examiner

*Primary Examiner* — Paul B Prebilic
(74) *Attorney, Agent, or Firm* — Oliff PLC (57) ABSTRACT

A first region is a circular region located at the centermost position. A first refractive power is uniformly added to the first region regardless of the distance from an axis of a lens part. A second region is a ring-like region located outside and adjacent to the first region. In the second region, a refractive power is increased or decreased from the first refractive power as the distance from the axis becomes larger. An outer region is a ring-like region located outside the second region. A reference refractive power for focusing on a far point is added to the outer region. An MTF curve at spatial frequency of 50 lp/mm relating to light passing through a region having a radius of 1.5 mm around the axis has one maximal value and no minimal value in a range of a defocusing value of −0.5 D to 0.5 D.

11 Claims, 6 Drawing Sheets

INTRAOCULAR LENS

CROSS REFERENCE TO RELATED APPLICATION

This application is based upon and claims the benefit of priority of Japanese Patent Application Nos. 2021-111586 filed on Jul. 5, 2021, 2021-111587 filed on Jul. 5, 2021, 2022-034885 filed on Mar. 8, 2022, 2022-034886 filed on Mar. 8, 2022, the contents of which are incorporated herein by reference in its entirety.

BACKGROUND

The present disclosure relates to an intraocular lens to be inserted into an eye.

As an intraocular lens to be inserted into an eye, an intraocular lens has been known that collects the incident light that is incident on a lens part, to a single focal point. According to the intraocular lens that collects the incident light to a single focal point, an object can be easily seen at high resolution, compared to an intraocular lens that collects the incident light that is incident on a lens part, to multiple focal points.

Further, a technique that realizes an appropriate resolution even in a case in which defocus is caused to some extent has been proposed. For example, Japanese Patent Application Publication No. 2004-121433 discloses an intraocular lens that expands the depth of focus (focal depth) by forming at least one surface of the lens part to be non-spherical shape, so that the deterioration of the resolution is suppressed even in the defocus.

SUMMARY

The first aspect to be solved by the present disclosure is now described. It has been found based on various simulation and examination that a large amount of light is not recognized by a wearer, among the light passing through the lens part to the retina in a case in which a method for expanding the depth of focus of the intraocular lens is inappropriate. In a case in which a large amount of light is not recognized by a wearer, a superior field of vision (visual field) is hardly obtained. Thus, it is desired to expand the depth of focus of the intraocular lens using an appropriate method.

The second aspect to be solved by the present disclosure is now described. It has been found based on various simulation and examination that a superior field of vision is hardly obtained in a case in which a method for expanding the depth of focus of the intraocular lens is inappropriate. For example, a method may be considered that adds different refractive powers to a peripheral portion and a center portion of the lens part so as to expand the depth of focus. However, a radius of a pupil of a human being varies in a range of approximately 1-8 mm. In the method that adds different refractive powers to the peripheral portion and the center portion of the lens part, when the pupil of a wearer becomes small, a rate of light passing through the peripheral portion of the lens part to the retina becomes small, compared to a case in which the pupil is large. Accordingly, when the pupil becomes small, a superior field of vision corresponding to the refractive power in the peripheral portion of the lens part is hardly obtained.

Embodiments of the broad principles derived herein provide an intraocular lens that decreases an amount of light, which is not recognized by a wearer, among the light passing through the lens part and that appropriately expands the depth of focus. Further, embodiments of the broad principles derived herein provide an intraocular lens that causes a superior field of vision regardless of a change of the size of the pupil of a wearer.

Embodiments of a first aspect provide an intraocular lens including a lens part. The lens part includes regions each having a circular or ring-like shape, the regions being disposed concentrically around an axis of the lens part. The regions in the lens part include: a first region that is a circular region located at the centermost position, a first refractive power being uniformly added to the first region regardless of the distance from the axis; a second region that is a ring-like region located adjacent to the first region at an outer side of the first region, a refractive power that is increased or decreased from the first refractive power as the distance from the axis becomes larger, being added to the second region; and an outer region that is a ring-like region located at an outer side of the second region, a reference refractive power for focusing on a far point being added to the outer region. An MTF curve at spatial frequency of 50 lp/mm relating to light passing through a region having a radius of 1.5 mm around the axis of the lens part has one maximal value and no minimal value in a range of a defocusing value of −0.5 D to 0.5 D.

Embodiments of a second aspect provide an intraocular lens including a lens part. The lens part includes regions each having a circular or ring-like shape, the regions being disposed concentrically around an axis of the lens part. The regions in the lens part include: a first region that is a circular region located at the centermost position, a first refractive power being added to the first region; a second region that is a ring-like region located adjacent to the first region at an outer side of the first region; a third region that is a ring-like region located adjacent to the second region at an outer side of the second region, a third refractive power that is different from the first refractive power being added to the third region; a fourth region that is a ring-like region located adjacent to the third region at an outer side of the third region; and an outer region that is a ring-like region located at an outer side of the fourth region, a reference refractive power for focusing on a far point being added to the outer region. In the second region, the refractive power is increased or decreased from the first refractive power in the first region to the third refractive power in the third region as the distance from the axis becomes larger. In the fourth region, the refractive power is decreased or increased to be opposite to the change of the refractive power in the second region, as the distance from the axis becomes larger. The first region, the second region, the third region, and at least a part of the fourth region are arranged within a region having a radius of 1.5 mm around the axis of the lens part. An MTF curve at spatial frequency of 50 lp/mm relating to light passing through a region having a radius of 1.5 mm around the axis of the lens part has one maximal value and no minimal value in a range of a defocusing value of −0.5 D to 0.5 D.

DETAILED DESCRIPTION

An intraocular lens provided by a typical embodiment of the present disclosure includes a lens part. The lens part includes regions each having a circular or ring-like shape, the regions being disposed concentrically around an axis of the lens part. The regions in the lens part include: a first region that is a circular region located at the centermost position, a first refractive power being uniformly added to the first region regardless of the distance from the axis; a second region that is a ring-like region located adjacent to the first region at an outer side of the first region, a refractive power that is increased or decreased from the first refractive power as the distance from the axis becomes larger, being added to the second region; and an outer region that is a ring-like region located at an outer side of the second region, a reference refractive power for focusing on a far point being added to the outer region. An MTF curve at spatial frequency of 50 lp/mm relating to light passing through a region having a radius of 1.5 mm around the axis of the lens part has one maximal value and no minimal value in a range of a defocusing value of −0.5 D to 0.5 D.

In addition or in the alternative to the preceding embodiment, a change rate of an area of the second region relative to an area of the first region may be set within a range of ±50%.

In addition or in the alternative to the preceding embodiments, an area of each of the first region and the second region may be 0.6 mm² or more.

In addition or in the alternative to the preceding embodiments, the first refractive power added to the first region may be a strong refractive power stronger than the reference refractive power. Further, the refractive power added to the second region may be decreased from the strong refractive power in the first region as the distance from the axis becomes larger.

In addition or in the alternative to the preceding embodiments, the regions in the lens part may further include: a third region that is a ring-like region located adjacent to the second region at an outer side of the second region, the reference refractive power being added to the third region; a fourth region that is a ring-like region located adjacent to the third region at an outer side of the third region; a fifth region that is a ring-like region located adjacent to the fourth region at an outer side of the fourth region, the strong refractive power being added to the fifth region; and a sixth region that is a ring-like region located adjacent to the fifth region at an outer side of the fifth region and located adjacent to the outer region at an inner side of the outer region. In the fourth region, the refractive power may be increased from the reference refractive power in the third region to the strong refractive power in the fifth region as the distance from the axis becomes larger. In the sixth region, the refractive power may be decreased from the strong refractive power in the fifth region to the reference refractive power in the outer region as the distance from the axis becomes larger.

In addition or in the alternative to the preceding embodiments, a change rate of an area of any region relative to an area of another region among the first region, the second region, the third region, the fourth region, the fifth region and the sixth region may be set within a range of ±50%.

In addition or in the alternative to the preceding embodiments, the area of each of the first region, the second region, the third region, the fourth region, the fifth region and the sixth region may be set to 0.6 mm² or more.

In addition or in the alternative to the preceding embodiments, the first region, the second region, the third region and at least a part of the fourth region may be arranged within a region having a radius of 1.5 mm around the axis of the lens part.

In addition or in the alternative to the preceding embodiments, the first region, the second region and at least a part of the third region may be arranged within a region having a radius of 1.0 mm around the axis of the lens part.

In addition or in the alternative to the preceding embodiments, the first region, the second region, the third region, the fourth region, the fifth region and at least a part of the sixth region may be arranged within a region having a radius of 1.5 mm around the axis of the lens part.

In addition or in the alternative to the preceding embodiments, the regions in the lens part may further include: a third region that is a ring-like region located adjacent to the second region at an outer side of the second region, a third refractive power different from the first refractive power being added to the third region; and a fourth region that is a ring-like region located adjacent to the third region at an outer side of the third region. The first refractive power added to the first region may be the reference refractive power. The third refractive power added to the third region may be a strong refractive power stronger than the reference refractive power. In the second region, the refractive power may be increased from the reference refractive power in the first region to the strong refractive power in the third region as the distance from the axis becomes larger. The outer region may be located adjacent to the fourth region at an outer side of the fourth region. In the fourth region, the refractive power may be decreased from the strong refractive power in the third region to the reference refractive power in the outer region as the distance from the axis becomes larger.

According to the intraocular lens of the typical embodiment of the present disclosure, the depth of focus can be appropriately expanded while decreasing an amount of light that is not recognized by a wearer among the light passing through the lens part.

An intraocular lens provided by another typical embodiment of the present disclosure includes a lens part including regions each having a circular or ring-like shape, the regions being disposed concentrically around an axis of the lens part. The regions in the lens part include: a first region that is a circular region located at the centermost position, a first refractive power being added to the first region; a second region that is a ring-like region located adjacent to the first region at an outer side of the first region; a third region that is a ring-like region located adjacent to the second region at an outer side of the second region, a third refractive power that is different from the first refractive power being added to the third region; a fourth region that is a ring-like region located adjacent to the third region at an outer side of the third region; and an outer region that is a ring-like region located at an outer side of the fourth region, a reference refractive power for focusing on a far point being added to the outer region. In the second region, the refractive power is increased or decreased from the first refractive power in the first region to the third refractive power in the third region as the distance from the axis becomes larger. In the fourth region, the refractive power is decreased or increased to be opposite to the change of the refractive power in the second region, as the distance from the axis becomes larger. The first region, the second region, the third region, and at least a part of the fourth region are arranged within a region having a radius of 1.5 mm around the axis of the lens part. An MTF curve at spatial frequency of 50 lp/mm relating to light passing through a region having a radius of 1.5 mm around the axis of the lens part has one maximal value and no minimal value in a range of a defocusing value of −0.5 D to 0.5 D.

In addition or in the alternative to the preceding embodiments, the third refractive power added to the third region may be the reference refractive power. The first refractive power added to the first region may be a strong refractive power stronger than the reference refractive power. In the second region, the refractive power may be decreased from the strong refractive power in the first region to the reference refractive power in the third region as the distance from the axis becomes larger. In the fourth region, the refractive power may be increased from the reference refractive power in the third region as the distance from the axis becomes larger.

In addition or in the alternative to the preceding embodiments, the first region, the second region and at least a part of the third region may be arranged within a region having a radius of 1.0 mm around the axis of the lens part.

In addition or in the alternative to the preceding embodiments, the regions in the lens part may further includes: a fifth region that is a ring-like region located adjacent to the fourth region at an outer side of the fourth region, the strong refractive power being added to the fifth region; and a sixth region that is a ring-like region located adjacent to the fifth region at an outer side of the fifth region and located adjacent to the outer region at an inner side of the outer region. In the sixth region, the refractive power may be decreased from the strong refractive power in the fifth region to the reference refractive power in the outer region as the distance from the axis becomes larger.

In addition or in the alternative to the preceding embodiments, the first region, the second region, the third region, the fourth region, the fifth region and at least a part of the sixth region may be arranged within a region having a radius of 1.5 mm around the axis of the lens part.

In addition or in the alternative to the preceding embodiments, the first refractive power added to the first region may be the reference refractive power. The third refractive power added to the third region may be a strong refractive power stronger than the reference refractive power. In the second region, the refractive power may be increased from the reference refractive power in the first region to the strong refractive power in the third region as the distance from the axis becomes larger. The outer region may be located adjacent to the fourth region at an outer side of the fourth region. In the fourth region, the refractive power may be decreased from the strong refractive power in the third region to the reference refractive power in the outer region as the distance from the axis becomes larger.

In addition or in the alternative to the preceding embodiments, the first region, the second region and at least a part of the third region may be arranged within a region having a radius of 1.0 mm around the axis of the lens part.

According to the intraocular lens of another typical embodiment of the present disclosure, the depth of focus is appropriately expanded, and a superior field of vision can be easily obtained regardless of the change of the size of the pupil of a wearer.

In the intraocular lens of a first aspect exemplarily described in the present disclosure, the regions each having a circular or ring-like shape (one circular region and one or more ring-like regions), are disposed in the lens part concentrically around an axis of the lens part. The regions include the first region, the second region and the outer region. The first region is a circular region located at the centermost position. The first refractive power is uniformly added to the first region regardless of the distance from the axis. The second region is a ring-like region located adjacent to the first region at an outer side of the first region. The refractive power that is increased or decreased from the first refractive power as the distance from the axis becomes larger, is added to the second region. The outer region is a ring-like region located at an outer side of the second region. The reference refractive power for focusing on a far point is added to the outer region. The MTF curve at spatial frequency of 50 lp/mm relating to light passing through a region having a radius of 1.5 mm around the axis of the lens part has one maximal value and no minimal value in a range of a defocusing value of −0.5 D to 0.5 D, as the position of which the MTF becomes the maximum is defined as a reference (0 D).

For example, it may be designed that the refractive power becomes strong as being closer to the axis in the center portion of the lens part so as to expand the depth of focus of the intraocular lens. However, in such a case, an amount of light that passes through a portion of which the refractive power becomes the maximum (a portion around the axis) is extremely small. Accordingly, a wearer cannot recognize the light passing through the portion around the axis and thus cannot recognize the field of vision corresponding to the maximum refractive power. Such a problem may also cause in a design in which the refractive power becomes small as being closer to the axis in the center portion of the lens part. In such designs, the light passing through the portion around the axis is not recognized by a wearer and thus loss of light might cause.

On the other hand, the intraocular lens exemplarily described in the present disclosure has the first region, the second region and the outer region and fulfills the requirement for intraocular lenses that collects much incident light that is incident on the lens part, in the vicinity of a specified focal point (in the following embodiments, a single focal point), so that the depth of focus of the intraocular lens is expanded. The requirement for intraocular lenses is that the MTF curve at spatial frequency of 50 lp/mm has one maximal value and no minimal value in a range of a defocusing value of −0.5 D to 0.5 D, as the position of which the MTF becomes the maximum is defined as a reference (0 D). Here, the first refractive power is uniformly added to the first region located at the centermost position, regardless of the distance from the axis. Thus, a wearer can appropriately recognize a field of vision corresponding to the first refractive power, compared to a configuration in which the refractive power is changed (namely, decreased or increased) at a position slightly apart from the axis O. Accordingly, an amount of light that is not recognized by a wearer is decreased, so that a superior field of vision can be easily obtained. Further, a wearer can also obtain the field of vision corresponding to the range of the refractive power closer to the first refractive power, using the light passing through the second region. Consequently, according to the technique of the present disclosure, the depth of focus can be appropriately expanded while decreasing an amount of the light that is not recognized by a wearer, among the light passing through the lens part.

The range of the defocusing value in which the above-describe MTF curve has one maximal value and no minimal value, may be changed. For example, the MTF curve may have one maximal value and no minimal value in a range of the defocusing value of −1.0 D to 0.5 D. Or alternatively, the MTF curve may have one maximal value and no minimal value in a range of the defocusing value of −1.5 D to 0.5 D. In these cases, the intraocular lens can be realized that the field of vision is hardly deteriorated even in a case in which defocus is largely caused.

The description of "the refractive power is uniformly added to a region regardless of the distance from the axis" used in the present disclosure is not limited to a configuration in which the refractive power is strictly uniform within the region. That is, the scope of the invention of the present disclosure also encompasses a configuration in which the refractive power slightly varies within the region in order for correction of the aberration or the like. For example, a change rate of the refractive power within the region (for example, a ratio of the maximum value to the minimum value of the refractive power within the region) may be within a range of ±15%, preferably a range of ±10%. Further, the reference refractive power added to the outer region may vary to some extent within the outer region in order for the correction of the aberration or the like.

A change rate of the area of the second region relative to the area of the first region may be set within a range of ±50%. That is, "(the area of the second region)/(the area of the first region)≤1±0.5" is fulfilled. In this case, the area of each of the first region and the second region is sufficiently secured. As a result, both of the field of vision corresponding to the first refractive power and the field of vision corresponding to the range of the refractive power closer to the first refractive power are further appropriately and easily obtained.

The above-described change rate of ±50% may be changed. For example, the change rate of the area of the second region relative to the area of the first region is set within a range of ±30%, so that the area of each of the first region and the second region can be further appropriately secured.

The area of each of the first region and the second region may be set to 0.6 mm$^2$ or more. In this case, the area of each of the first region and the second region is sufficiently secured. As a result, both of the field of vision corresponding to the first refractive power and the field of vision corresponding to the range of the refractive power closer to the first refractive power are further appropriately and easily obtained.

The area of each of the first region and the second region may be 0.8 mm$^2$ or more, preferably 1.1 mm$^2$ or more. In this case, the area of each of the first region and the second region can be further appropriately secured.

The area of the second region may be larger than the area of the first region. In this case, the area of the second region in which the refractive power varies in response to the distance from the axis can be further appropriately secured. Thus, the field of vision corresponding to the refractive power closer to the first refractive power can be further appropriately obtained. That is, the depth of focus of the intraocular lens is further preferably deepened (expanded).

The first refractive power added to the first region may be a strong refractive power stronger than the reference refractive power. In the second region, the refractive power may be decreased from the strong refractive power in the first region as the distance from the axis becomes larger. In the intraocular lens, the aberration is hardly caused in the vicinity of the axis, compared to the peripheral portion of the lens part. As the refractive power is stronger, the aberration or the like largely affects the field of vision of a wearer. Thus, by adding the strong refractive power stronger than the reference refractive power to the first region that is a central region in which the aberration is hardly caused, the influence of the aberration or the like to the field of vision of a wearer can be decreased, compared to a configuration in which the reference refractive power is added to the first region.

The regions in the lens part may further include a third region, a fourth region, a fifth region and a sixth region. The third region is a ring-like region located adjacent to the second region at an outer side of the second region. The reference refractive power is added to the third region. The fourth region is a ring-like region located adjacent to the third region at an outer side of the third region. The fifth region is a ring-like region located adjacent to the fourth region at an outer side of the fourth region. The strong refractive power is added to the fifth region. The sixth region is a ring-like region located adjacent to the fifth region at an outer side of the fifth region and located adjacent to the outer region at an inner side of the outer region. In the fourth region, the refractive power is increased from the reference refractive power in the third region to the strong refractive power in the fifth region as the distance from the axis becomes larger. In the sixth region, the refractive power is decreased from the strong refractive power in the fifth region to the reference refractive power in the outer region as the distance from the axis becomes larger.

In this case, the strong refractive power region (the first region), the transition region (the second region), the reference refractive power region (the third region), the transition region (the fourth region), the strong refractive power region (the fifth region), the transition region (the sixth region), and the reference refractive power region (the outer region) are arranged in this order from the inner side toward the outer side. That is, two strong refractive power regions are arranged inside the ring-like outer region, and the reference refractive power region is arranged between the two strong refractive power regions. Thus, even when the pupil of a wearer is not largely expanded (namely, the pupil is smaller than the outer region), the light to the retina easily and appropriately passes through each of the strong refractive power region, the reference refractive power region, and the transition region. As a result, an appropriate field of vision can be further easily obtained regardless of the change of the size of the pupil of a wearer. Further, an increase of the aberration caused by increasing the number of regions can be suppressed, compared to a configuration having seven or more regions inside the outer region. The strong refractive power in the first region need not necessarily be strictly identical to the strong refractive power in the fifth region, which will be described in detail later. Further, the reference refractive power in the third region need not necessarily be strictly identical to the reference refractive power in the outer region.

A change rate of an area of any region relative to an area of another region among the first region, the second region, the third region, the fourth region, the fifth region and the sixth region may be set within a range of ±50%. In this case, the area of each of the first region to the sixth region is sufficiently secured. As a result, even when the pupil is smaller than the outer region, an appropriate field of vision corresponding to the range of the refractive power between the reference refractive power and the strong refractive power can be easily obtained. Further, similar to the above-described configuration, the change rate of ±50% may be changed. For example, the change rate of ±50% may be changed to a change rate of ±30%.

The area of each of the first region, the second region, the third region, the fourth region, the fifth region and the sixth region may be set to 0.6 mm$^2$ or more. In this case, the area of each of the first region to the sixth region is sufficiently secured. As a result, even when the pupil is smaller than the outer region, an appropriate field of vision corresponding to the range of the refractive power between the reference refractive power and the strong refractive power can be easily obtained. Further, as described above, the area of 0.6 mm$^2$ or more may be changed. For example, the area of each region may be set to 0.8 mm$^2$ or more, preferably 1.1 mm$^2$ or more.

The area of the fourth region may be larger than the area of the third region. The area of the sixth region may be larger than the area of the fifth region. In this case, the field of vision corresponding to the refractive power between the reference refractive power and the strong refractive power can be further appropriately obtained. Thus, the depth of focus of the intraocular lens is further preferably deepened.

At least a part of a configuration of an intraocular lens of a second aspect described below may be added to the configuration of the intraocular lens of the above-described first aspect. Further, at least a part of the configuration of the intraocular lens of the first aspect may be added to the configuration of the intraocular lens of the second aspect.

In the intraocular lens of a second aspect exemplarily described in the present disclosure, the regions each having a circular or ring-like shape (one circular region and one or more ring-like regions), are disposed in the lens part concentrically around an axis of the lens part. The regions in the lens part include a first region, a second region, a third region, a fourth region and an outer region. The first region is a circular region located at the centermost position. A first refractive power is added to the first region. The second region is a ring-like region located adjacent to the first region at an outer side of the first region. The third region is a ring-like region located adjacent to the second region at an outer side of the second region. A third refractive power that is different from the first refractive power is added to the third region. The fourth region is a ring-like region located adjacent to the third region at an outer side of the third region. The outer region is a ring-like region located at an outer side of the fourth region. A reference refractive power for focusing on a far point is added to the outer region. In the second region, the refractive power is increased or decreased from the first refractive power in the first region to the third refractive power in the third region as the distance from the axis becomes larger. In the fourth region, the refractive power is decreased or increased to be opposite to the change of the refractive power in the second region, as the distance from the axis becomes larger. The first region, the second region, the third region, and at least a part of the fourth region are arranged within a region having a radius of 1.5 mm around the axis of the lens part. An MTF curve at spatial frequency of 50 lp/mm relating to light passing through a region having a radius of 1.5 mm around the axis of the lens part has one maximal value and no minimal value in a range of a defocusing value of −0.5 D to 0.5 D, as the position of which the MTF becomes the maximum is defined as a reference (0 D).

The intraocular lens exemplarily described in the present disclosure has the first region, the second region, third region and the fourth region in this order from the center of the intraocular lens and fulfills the requirement for intraocular lenses that collects much incident light that is incident on the lens part, in the vicinity of a specified focal point (in the following embodiments, a single focal point), so that the depth of focus of the intraocular lens is expanded. The requirement for intraocular lenses is that the MTF curve at spatial frequency of 50 lp/mm has one maximal value and no minimal value in a range of a defocusing value of −0.5 D to 0.5 D, as the position of which the MTF becomes the maximum is defined as a reference (0 D). Here, the first refractive power added to the first region is different from the third refractive power added to the third region. The refractive power in the second region varies to be opposite to the change of the refractive power in the fourth region as the distance from the axis becomes larger. Further, the first region the second region, the third region and at least a part of the fourth region are arranged within a region having a radius of 1.5 mm corresponding to a radius of the pupil of a human being in a state in which the pupil is contracted to some extent. Thus, even when the pupil of a wearer is contracted to some extent, the light to the retina passes through each of the first region to which the first refractive power is added, the third region to which the third refractive power is added, and the transition regions (the second region and the fourth region) in which the refractive power varies between the first refractive power and the third refractive power. Accordingly, an appropriate field of vision corresponding to a range of the refractive power between the first refractive power and the third refractive power can be easily obtained regardless of a change of the size of the pupil of a wearer.

The range of the defocusing value in which the above-describe MTF curve has one maximal value and no minimal value, may be changed. For example, the MTF curve may have one maximal value and no minimal value in a range of the defocusing value of −1.0 D to 0.5 D. Or alternatively, the MTF curve may have one maximal value and no minimal value in a range of the defocusing value of −1.5 D to 0.5 D. In these cases, the intraocular lens can be realized that the field of vision is hardly deteriorated even in a case in which defocus is largely caused.

The third refractive power added to the third region may be a reference refractive power for focusing on a far point. The first refractive power added to the first region may be a strong refractive power stronger than the reference refractive power. In the second region, the refractive power may be decreased from the strong refractive power in the first region to the reference refractive power in the third region as the distance from the axis becomes larger. In the fourth region, the refractive power may be increased from the reference refractive power in the third region as the distance from the axis becomes larger.

In the intraocular lens the aberration is hardly caused in the vicinity of the axis, compared to the peripheral portion of the lens part. As the refractive power is stronger, the aberration or the like largely affects the field of vision of a wearer. Thus, by adding the strong refractive power stronger than the reference refractive power to the first region that is a central region in which the aberration is hardly caused, the influence of the aberration or the like to the field of vision of a wearer can be decreased, compared to a configuration in which the reference refractive power is added to the first region.

The reference refractive power added to the third region need not necessarily be strictly identical to the reference refractive power added to the outer region. For example, a change rate of the reference refractive power in the third region relative to the reference refractive power in the outer region may be set within a range of ±30% (namely, "the reference refractive power in the third region"/"the reference refractive power in the outer region"≤1±0.3), preferably a range of ±20%. Also in this case, an appropriate field of vision can be obtained regardless of the change of the size of the pupil of a wearer. However, in a case in which the reference refractive power in the third region is closer to the reference refractive power in the outer region, the field of vision for a far point when the pupil of a wearer is contracted to some extent can be easily obtained.

The first region, the second region and at least a part of the third region may be arranged within a region having a radius of 1.0 mm around the axis of the lens part. In a light environment, the pupil of a human being is contracted to a radius of approximately 1.0 mm or less. In a case in which the first region, the second region, and at least a part of the third region are arranged within a region having a radius of 1.0 mm around the axis, the light to the retina passes through each of the first region, the second region, and the third region even in the light environment. Thus, even when the pupil of a wearer is contracted to be extremely small, an appropriate field of vision corresponding to the range of the refractive power between the reference refractive power and the strong refractive power can be easily obtained.

The regions in the lens part may further include a fifth region and a sixth region. The fifth region is a ring-like region located adjacent to the fourth region at an outer side of the fourth region. The strong refractive power is added to the fifth region. The sixth region is a ring-like region located adjacent to the fifth region at an outer side of the fifth region and located adjacent to the outer region at an inner side of the outer region. In the sixth region, the refractive power is decreased from the strong refractive power in the fifth region to the reference refractive power in the outer region as the distance from the axis becomes larger. In this case, the strong refractive power region (the first region), the transition region (the second region), the reference refractive power region (the third region), the transition region (the fourth region), the strong refractive power region (the fifth region), the transition region (the sixth region), and the reference refractive power region (the outer region) are arranged in this order from the inner side toward the outer side. That is, two strong refractive power regions are arranged inside the ring-like outer region, and the reference refractive power region is arranged between the two strong refractive power regions. Thus, even when the pupil of a wearer is not largely expanded, the light to the retina easily and appropriately passes through each of the strong refractive power region, the reference refractive power region, and the transition region. As a result, an appropriate field of vision can be further easily obtained regardless of the change of the size of the pupil of a wearer. Further, an increase of the aberration caused by increasing the number of regions can be suppressed, compared to a configuration having seven or more regions inside the outer region.

The first region, the second region, the third region, the fourth region, the fifth region and at least a part of the sixth region may be arranged within a region having a radius of 1.5 mm around the axis of the lens part. In this case, even when the pupil of a wearer is contracted to some extent, the light to the retina passes through each of the two strong refractive power regions, the reference refractive power region therebetween, and the three transition regions. Accordingly, an appropriate field of vision corresponding to a range of the refractive power between the reference refractive power and the strong refractive power can be easily obtained regardless of the change of the size of the pupil of a wearer.

The strong refractive power added to the first region need not necessarily be strictly identical to the strong refractive power added to the fifth region. For example, a change rate of the strong refractive power in the first region relative to the strong refractive power in the fifth region may be set within a range of ±30% (preferably ±20%). Also in this case, an appropriate field of vision can be obtained regardless of the change of the size of the pupil of a wearer.

The refractive power added to the fifth region may be closer to the strong refractive power added to the first region rather than the reference refractive power added to the outer region. Also in this case, an appropriate field of vision can be obtained regardless of the change of the size of the pupil of a wearer.

However, in a configuration in which the strong refractive power is added to the first region and the reference refractive power is added to the third region, a configuration of other region may be changed. For example, the fifth region between the fourth region and the sixth region may be omitted. Also in this case, a field of vision corresponding to a range of the refractive power between the reference refractive power and the strong refractive power can be obtained.

The first refractive power added to the first region may be a reference refractive power for focusing on a far point. The third refractive power added to the third region may be a strong refractive power stronger than the reference refractive power. In the second region, the refractive power may be increased from the reference refractive power in the first region to the strong refractive power in the third region as the distance from the axis becomes larger. The outer region may be located adjacent to the fourth region at an outer side of the fourth region. In the fourth region, the refractive power may be decreased from the strong refractive power in the third region to the reference refractive power in the outer region as the distance from the axis becomes larger. In this case, the number of the regions arranged inside the outer region is four which is as small as possible. As the number of the regions becomes small, an amount of the aberration is easily suppressed. Thus, by setting the number of the regions arranged inside the outer region to four, an appropriate field of vision can be easily obtained regardless of the size of the pupil of a wearer while restricting the aberration from causing.

The reference refractive power added to the first region need not necessarily be strictly identical to the reference refractive power added to the outer region. For example, a change rate of the reference refractive power in the first region relative to the reference refractive power in the outer region may be set within a range of ±30% (preferably ±20%).

The first region, the second region and at least a part of the third region may be arranged within a region having a radius of 1.0 mm around the axis of the lens part. As described above, in a light environment, the pupil of a human being is contracted to a radius of approximately 1.0 mm or less. In a case in which the first region, the second region, and at least a part of the third region are arranged within a region having a radius of 1.0 mm around the axis, the light to the retina passes through each of the first region, the second region, and the third region even in an extremely light environment. Thus, even when the pupil of a wearer is contracted to be extremely small, an appropriate field of vision corresponding to the range of the refractive power between the reference refractive power and the strong refractive power can be easily obtained.

FIRST EMBODIMENT (General Configuration)

An intraocular lens 1 of the first embodiment is now described with reference to FIG. 1 to FIG. 5. First, a general configuration of the intraocular lens 1 is described with reference to FIG. 1. The general configuration of the intraocular lens 1 described below is common to that of the intraocular lens of the second embodiment described later. In each of the first embodiment and the second embodiment, an intraocular lens (a so-called single focal intraocular lens) that collects the incident light that is incident on a lens part 2, in the vicinity of a single focal point is exemplarily described. However, an intraocular lens to which the technique of the present disclosure is applied may be any intraocular lens of which an MTF (Modulation Transfer Function) curve at spatial frequency of 50 lp/mm has one maximal value and no minimal value in a range of a defocusing value of −0.5 D to 0.5 D. Accordingly, the technique of the present disclosure may be applied to various intraocular lenses (for example, a multifocal intraocular lens) other than a single focal intraocular lens.

Figure 1:
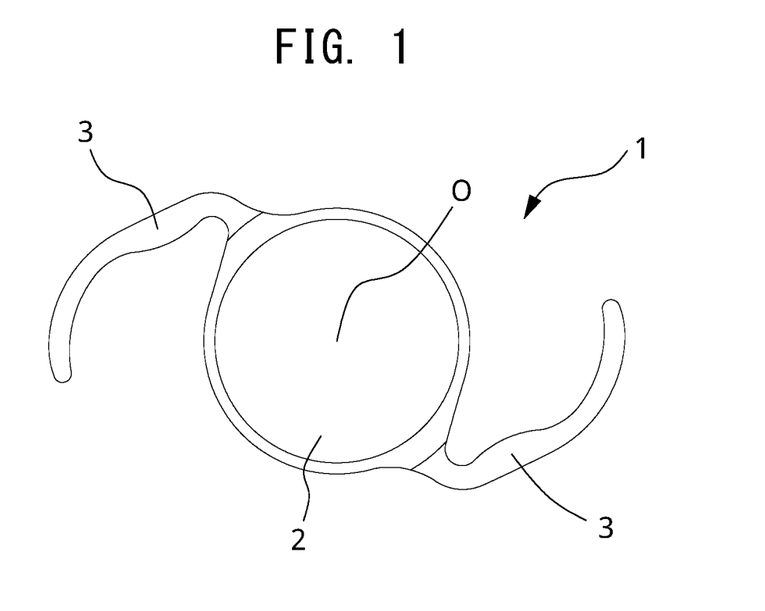
FIG. 1 is a plane view of an intraocular lens 1.

The intraocular lens 1 includes the lens part (optical part) 2 and a support part 3. The intraocular lens 1 of this embodiment is a so-called one-piece type intraocular lens in which the lens part 2 and the support part 3 are integrally formed to each other. However, the technique exemplarily disclosed in the present disclosure may be also applied to an intraocular lens (for example, a three-piece type intraocular lens) other than the one-piece type intraocular lens. As examples of the material of the intraocular lens 1, each of butylacrylate (BA) and hydroxyethyl methacrylate (HEMA) may be employed alone, or various soft materials such as a composite material of acrylic ester and methacrylic ester may be employed.

The lens part 2 is configured to impart a specified refractive power to a subject eye. A pair of lens surfaces (front surface and rear surface) of the lens part 2 is each formed as a convex surface. The lens part 2 has an axis O that is orthogonal to a lens surface and passes the center of the lens part 2. In this embodiment, the axis O of the lens part 2 matches with an optical axis of the lens part 2.

In the intraocular lens 1 of this embodiment, at least one of the lens surfaces in the lens part 2 is formed in a non-spherical shape, so that the refractive power of each portion in the lens part 2 is adjusted. As one example, in this embodiment, the front surface (convex surface) of the lens part 2 is formed in a non-spherical shape, so that the refractive power of each portion in the lens part 2 is adjusted. However, the rear surface or both of the front surface and the rear surface of the lens part 2 may be formed in a non-spherical shape. For example, a surface opposite to the surface formed in a non-spherical shape for realizing the refractive power described below, among the front surface and the rear surface of the lens part 2 may be formed in a toric shape for correcting astigmatism. In this case, an effect that corrects the astigmatism can be realized in addition to the effect of the intraocular lens 1 described in this embodiment.

The support part 3 is configured to support the lens part 2 in an eye (in this embodiment, within a lens capsule) of a wearer. As one example, the intraocular lens 1 of this embodiment has a pair of the support parts 3. However, the number of the support parts 3 is not limited to two. In this embodiment, the shape of the support part 3 is a loop shape curved in a circumferential direction. A distal end of the support part 3 is formed as a free end.

(Regions in Lens Part)

Figure 2:
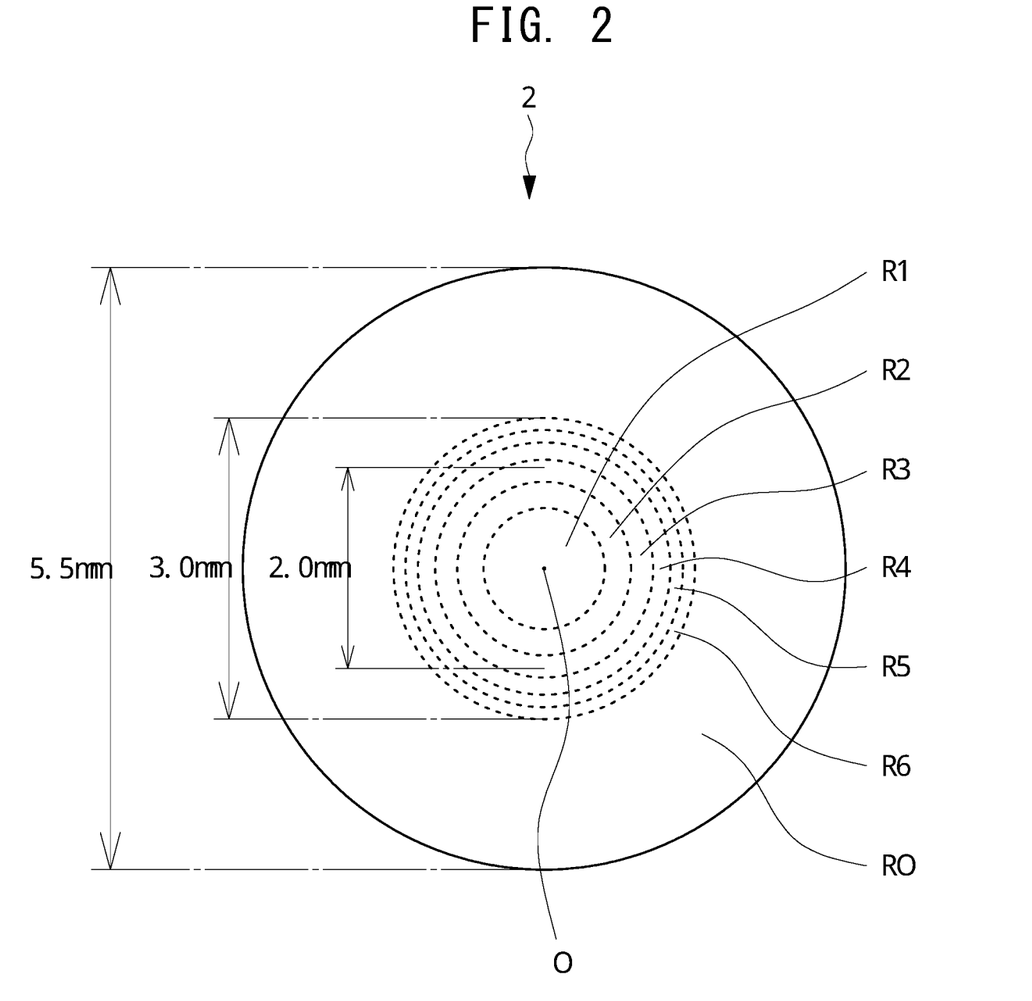
FIG. 2 is a schematic view illustrating a front surface of a lens part 2 in the intraocular lens of the first embodiment.

A detailed configuration of the lens part 2 in the intraocular lens 1 of the first embodiment is described with reference to FIG. 2. As shown in FIG. 2, when the lens part 2 is seen in a direction along the axis O (from the front side in FIG. 2), regions R1 to R6 and RO each having a circular shape or a ring shape are disposed concentrically in the lens part 2 around the axis O. As described above, in this embodiment, the front surface (convex surface) of the lens part 2 is formed in a non-spherical shape so as to dispose the regions R1 to R6 and RO.

The first region R1 is a circular region located at the centermost position among a plurality of the regions. Each of the second region R2, the third region R3, the fourth region R4, the fifth region R5, the sixth region R6, and the outer region RO is a ring-like region. The second region R2 is located adjacent to the first region R1 at an outer side of the first region R1. The third region R3 is located adjacent to the second region R2 at an outer side of the second region R2. The fourth region R4 is located adjacent to the third region R3 at an outer side of the third region R3. The fifth region R5 is located adjacent to the fourth region R4 at an outer side of the fourth region R4. The sixth region R6 is located adjacent to the fifth region R5 at an outer side of the fifth region R5. The outer region RO is located adjacent to the sixth region R6 at an outer side of the sixth region R6.

(Refractive Power in Each Region)

The refractive power in each of the regions R1 to R6 and RO in the lens part 2 of the first embodiment is described with reference to FIG. 3. In the graph shown in FIG. 3, a horizontal axis denotes a distance from the axis O in the lens part 2, and a vertical axis denotes the refractive power (diopter) of the lens part 2. In this embodiment, the refractive power added to the lens part 2 for a wearer for focusing on a far point is defined as a reference refractive power. In the graph, the reference refractive power is set to "0 D". As the refractive power to be added becomes stronger, the focal point on which a wearer focuses gets close to a near point.

The refractive power (first refractive power) added to the first region R1 is a strong refractive power stronger than the reference refractive power for focusing on a far point. Specifically, the strong refractive power is uniformly added to the first region R1 of this embodiment regardless of the distance from the axis O.

In the second region R2, the refractive power is decreased from the first refractive power, as the distance from the axis O becomes larger. Specifically, the refractive power in the second region R2 is decreased from the strong refractive power in the first region R1 to a third refractive power (i.e., the reference refractive power of 0 (D) in this embodiment) of the third region R3, as the distance from the axis O becomes larger. The refractive power in the second region R2 of this embodiment is decreased to be proportional to the distance from the axis O.

The refractive power (the third refractive power) added to the third region R3 is the reference refractive power. Specifically, the reference refractive power is uniformly added to the third region R3 of this embodiment regardless of the distance from the axis O.

In the fourth region R4, the refractive power is increased from the third refractive power, as the distance from the axis O becomes larger. Specifically, the refractive power in the fourth region R4 is increased from the reference refractive power in the third region R3 to a fifth refractive power (the strong refractive power) added to the fifth region R5, as the distance from the axis O becomes larger. The refractive power in the fourth region R4 of this embodiment is increased to be proportional to the distance from the axis O.

The refractive power (the fifth refractive power) added to the fifth region R5 is the strong refractive power. Specifically, the strong refractive power is uniformly added to the fifth region R5 of this embodiment regardless of the distance from the axis O. In this embodiment, the strong refractive power added to the first region R1 is identical to the strong refractive power added to the fifth region R5. However, the strong refractive power added to the first region R1 need not necessarily be strictly identical to the strong refractive power added to the fifth region R5. For example, a change rate of the strong refractive power in the fifth region R5 relative to the strong refractive power in the first region R1 may be set within a range of ±30% (preferably ±20%). Also in this case, an appropriate field of vision can be obtained regardless of the change of the size of the pupil of a wearer.

In the sixth region R6, the refractive power is decreased from the fifth refractive power, as the distance from the axis O becomes larger. Specifically, the refractive power in the sixth region R6 is decreased from the strong refractive power in the fifth region R5 to the reference refractive power added to the outer region RO, as the distance from the axis O becomes larger. The refractive power in the sixth region R6 of this embodiment is decreased to be proportional to the distance from the axis O.

The refractive power added to the outer region RO is the reference refractive power. Specifically, the reference refractive power is uniformly added to the outer region RO of this embodiment regardless of the distance from the axis O. However, the reference refractive power added to the outer region RO may vary within the outer region RO in order for correction of the aberration. In this embodiment, the reference refractive power added to the third region R3 is identical to the reference refractive power added to the outer region RO. However, the reference refractive power added to the third region R3 need not necessarily be strictly identical to the reference refractive power added to the outer region RO. For example, a change rate of the reference refractive power in the third region R3 relative to the reference refractive power in the outer region RO may be set within a range of ±30% (preferably ±20%). Also in this case, an appropriate field of vision can be obtained regardless of the change of the size of the pupil of a wearer.

In this embodiment, the region in which the refractive power is increased or decreased as the distance from the axis O becomes larger, among the regions R1 to R6 and RO (namely, the second region R2, the fourth region R4 and the sixth region R6) may be referred to as a transition region.

(Area of Each Region)

In this embodiment, a change rate of an area of any region relative to an area of another region among the first region R1, the second region R2, the third region R3, the fourth region R4, the fifth region R5 and the sixth region R6 is set within a range of ±50%. Specifically, in this embodiment, the lens part 2 is designed such that the areas of the first region R1 to the sixth region R6 are identical to each other.

Further, in this embodiment, the area of each of the first region R1, the second region R2, the third region R3, the fourth region R4, the fifth region R5 and the sixth region R6 is set to 0.6 mm² or more. Specifically, in this embodiment, the area of each of the first region R1 to the sixth region R6 is set to 1.1 mm² or more.

(Characteristic of MTF)

The characteristic of an MTF in the intraocular lens 1 of this embodiment is described with reference to FIG. 4 and FIG. 5. The MTF (Modulation Transfer Function) is an index that indicates a contrast. Each of the graphs in FIG. 4 and FIG. 5 shows an MTF curve at spatial frequency of 50 lp/mm having a defocusing value (an amount of defocus or power error) shown in a horizontal axis and the MTF shown in a vertical axis.

Figure 4:
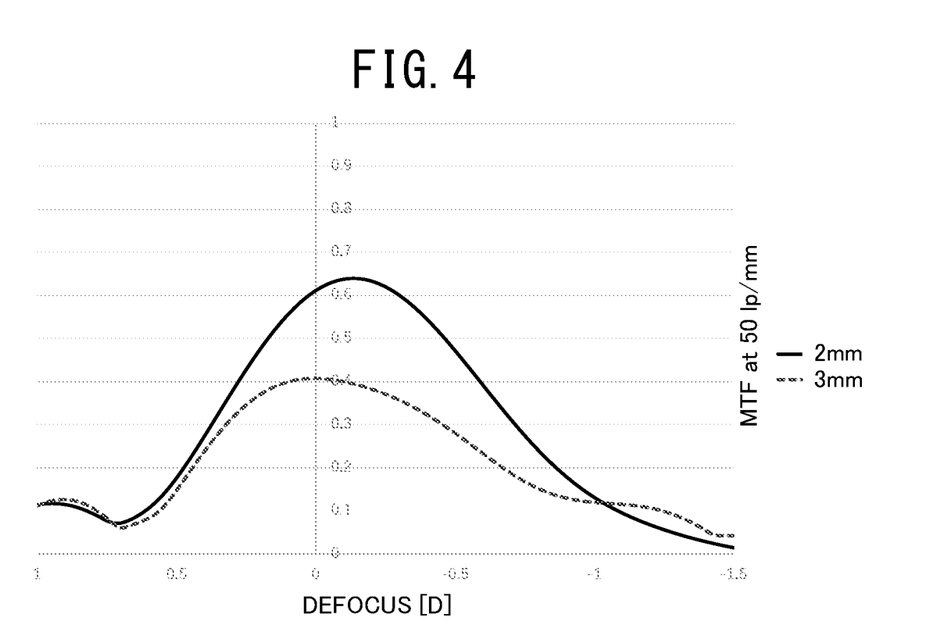
FIG. 4 is a graph comparing an MTF (Modulation Transfer Function) curve relating to the light passing through a region having a radius of 1.5 mm around the axis O of the lens part 2 and an MTF curve relating to the light passing through a region having a radius of 1.0 mm around the axis O of the lens part 2 of the first embodiment.
Figure 5:
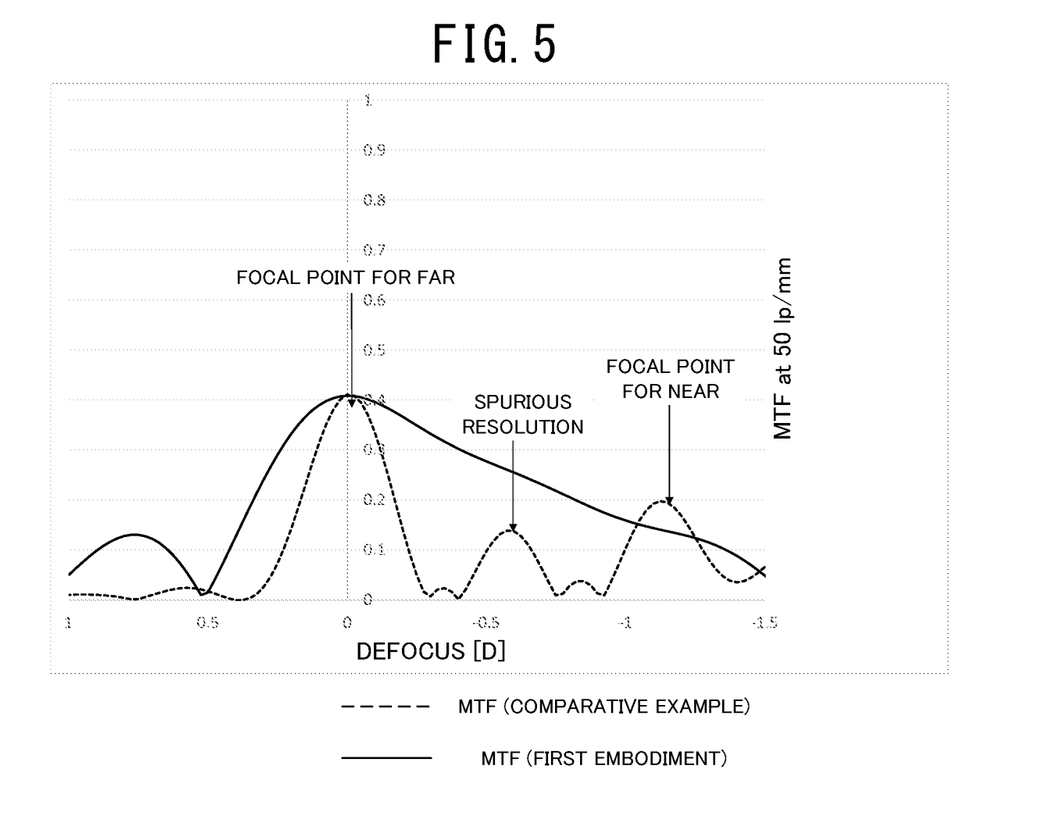
FIG. 5 is a graph comparing an MTF curve of the intraocular lens 1 of the first embodiment and an MTF curve of an intraocular lens of a comparative example.

FIG. 4 is a graph in an optical system simulating an eye of a wearer wearing the intraocular lens 1 of the first embodiment, the graph comparing an MTF curve relating to the light passing through a region having a radius of 1.5 mm (a diameter of 3.0 mm) around the axis O of the lens part 2 and an MTF curve relating to the light passing through a region having a radius of 1.0 mm (a diameter of 2.0 mm) around the axis O of the lens part 2. In the graph shown in FIG. 4, the MTF curve relating to the region having the radius of 1.5 mm (the diameter of 3.0 mm) is shown by a dotted line, and the MTF curve relating the region having the radius of 1.0 mm (the diameter of 2.0 mm) is shown by a solid line. The region having the radius of 1.5 mm (the diameter of 3.0 mm) around the axis O of the lens part 2 approximates to a region through which the light passes when the pupil of a wearer is contracted to some extent. Further, the region having the radius of 1.0 mm (the diameter of 2.0 mm) around the axis O of the lens part 2 approximates to a region through which the light passes when the pupil of a wearer is contracted to be extremely small.

As shown in FIG. 4, the intraocular lens 1 of the first embodiment fulfills the requirement for intraocular lenses that collects much incident light that is incident on the lens part 2, in the vicinity of a specified focal point (in this embodiment, a single focal point) even when the light passes through the region having the radius of 1.5 mm (the diameter of 3.0 mm) (namely, when the pupil of a wearer is contracted to some extent). The requirement for intraocular lenses is that the MTF curve at spatial frequency of 50 lp/mm has one maximal value and no minimal value in a range of a defocusing value of −0.5 D to 0.5 D (specifically, −1.5 D to 0.5 D) as the position of which the MTF becomes the maximum is defined as a reference (0 D). The MTF shows a large value not only around the maximal value, and the MTF keeps the large value even when the defocusing value is increased or decreased to some extent. That is, in the intraocular lens 1 of the first embodiment, the depth of focus is appropriately expanded.

Also, as shown in FIG. 4, the intraocular lens 1 fulfills the requirement for intraocular lenses that collects much incident light that is incident on the lens part 2, in the vicinity of a specified focal point (in this embodiment, a single focal point) even when the light passes through the region having the radius of 1.0 mm (the diameter of 2.0 mm) (namely, when the pupil of a wearer is contracted to be extremely small). Further, the depth of focus is appropriately expanded. The best focusing point in the region having the radius of 1.0 mm is different from the best focusing point in the region having the radius of 1.5 mm by only −0.15 D. Accordingly, a far vision is hardly deteriorated even when the pupil of a wearer is contracted to be extremely small.

FIG. 5 is a graph illustrating a result of simulation comparing the MTF curve of the intraocular lens 1 of the first embodiment and an MTF curve of an intraocular lens of a comparative example. In the intraocular lens of the comparative example, a strong refractive power added to each of the first region R1 and the fifth region R5 is different from that of the intraocular lens 1 of the first embodiment, and a change amount of the refractive power in each of the second region R2, the fourth region R4 and the sixth region R6 is different from that of the intraocular lens 1 of the first embodiment. Specifically, in the intraocular lens of the comparative example, the strong refractive power of approximately 2.4 D is added to the first region R1, and the strong refractive power of approximately 2.8 D is added to the fifth region R5. On the other hand, in the intraocular lens 1 of the first embodiment, the strong refractive power of 1.3 D is added to each of the first region R1 and the fifth region R5 (see FIG. 3). A region through which the light passes having the radius of 1.5 mm (the diameter of 3.0 mm) around the axis O is common to the first embodiment and the comparative example.

As shown in FIG. 5, in the intraocular lens of the comparative example, the strong refractive power added to each of the first region R1 and the fifth region R5 is largely increased from the strong refractive power in the intraocular lens 1 of the first embodiment, and thus a focal point for far and a focal point for near are formed. That is, the intraocular lens of the comparative example has a characteristic of multifocal intraocular lens and thus cannot collect much incident light that is incident on the lens part 2, in the vicinity of a single focal point. On the other hand, in the intraocular lens 1 of the first embodiment, the strong refractive power added to each of the first region R1 and the fifth region R5 is appropriately adjusted, so that the depth of focus is appropriately expanded while keeping a function that collects the incident light that is incident on the lens part 2, in the vicinity of a single focal point. In the graph of the comparative example, the peak shown between a focal point for far and a focal point for near is not a peak of a focal point for intermediate, but the peak is caused by a phenomenon of a spurious resolution.

(Decreasing of Loss of Light)

Figure 3:
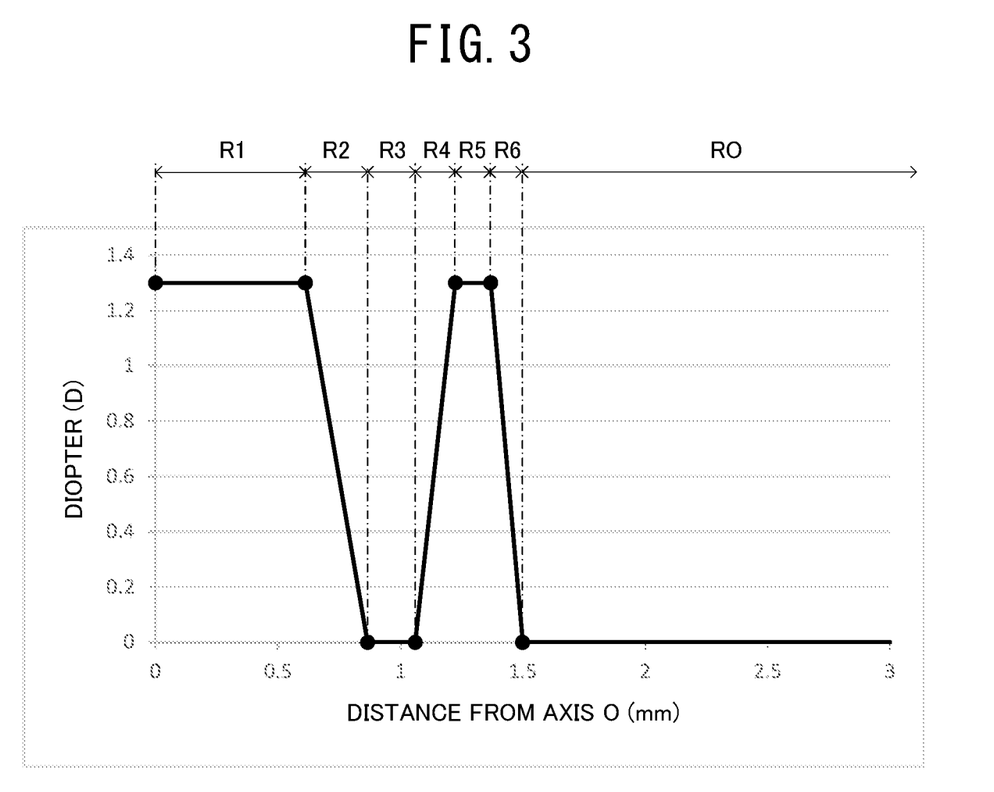
FIG. 3 is a graph illustrating a relation between a distance from an axis O of the lens part 2 of the first embodiment and a refractive power (diopter) of the lens part 2.

As shown in FIG. 3, the first refractive power (in this embodiment, the strong refractive power) is uniformly added to the first region R1 regardless of the distance from the axis O. Thus, a wearer can appropriately recognize a field of vision corresponding to the first refractive power, compared to a configuration in which the refractive power is decreased or increased at a position slightly apart from the axis O. Accordingly, an amount of light that is not recognized by a wearer is decreased, so that a superior field of vision can be easily obtained. Further, the wearer can also obtain the field of vision corresponding to the range of the refractive power closer to the first refractive power, using the light passing through the second region R2. Consequently, according to the technique of the present disclosure, the depth of focus can be appropriately expanded while decreasing an amount of the light that is not recognized by a wearer, among the light passing through the lens part 2.

A change rate of the area of the second region R2 relative to the area of the first region R1 is within a range of ±50%. As a result, the area of each of the first region R1 and the second region R2 is sufficiently secured. In the first embodiment, the area of each of the first region R1 and the second region R2 is set to 0.6 mm² or more, so that the area of each of the first region R1 and the second region R2 is sufficiently secured. Thus, both of the field of vision corresponding to the first refractive power and the field of vision corresponding to the range of the refractive power closer to the first refractive power are further appropriately and easily obtained.

The area of the second region R2 is equal to or larger than the area of the first region R1 (in this embodiment, the area of the second region R2 is equal to the area of the first region R1). As a result, the area of the second region R2 in which the refractive power varies in response to the distance from the axis O is appropriately secured. Thus, the field of vision corresponding to the range of the refractive power closer to the first refractive power is appropriately obtained. That is, the depth of focus of the intraocular lens 1 is further appropriately expanded.

As shown in FIG. 3, in the intraocular lens 1 of the first embodiment, the strong refractive power is added to the first region R1. Further, the refractive power in the second region R2 is decreased from the strong refractive power in the first region R1 as the distance from the axis O becomes larger. In the intraocular lens, the aberration is hardly caused in a portion near the axis O, compared to a peripheral portion of the lens part 2. Further, as the refractive power is stronger, an influence to the field of vision of a wearer caused by the aberration or the like becomes larger. Thus, the strong refractive power stronger than the reference refractive power is added to the first region R1, which is a region near the center portion that hardly causes the aberration, so that the influence to the field of vision of a wearer caused by the aberration or the like is decreased, compared to a configuration in which the reference refractive power is added to the first region R1.

As shown in FIG. 2 and FIG. 3, in the first embodiment, the strong refractive power region (the first region R1), the transition region (the second region R2), the reference refractive power region (the third region R3), the transition region (the fourth region R4), the strong refractive power region (the fifth region R5), the transition region (the sixth region R6), and the reference refractive power region (the outer region RO) are arranged in this order from the inner side toward the outer side. That is, two strong refractive power regions are arranged inside the ring-like outer region RO, and the reference refractive power region is arranged between the two strong refractive power regions. Thus, in a case in which the pupil is smaller than the outer region RO, the light to the retina easily and appropriately passes through each of the strong refractive power region, the reference refractive power region, and the transition region. As a result, an appropriate field of vision is further easily obtained. Further, an increase of the aberration caused by increasing the number of regions can be suppressed, compared to a configuration having seven or more regions inside the outer region RO. Further, similar to the first region R1, the strong refractive power is uniformly added to the fifth region R5 regardless of the distance from the axis O. Thus, the field of vision corresponding to the strong refractive power is appropriately obtained. In other words, an amount of light that is not recognized by a wearer is appropriately decreased.

A change rate of an area of any region relative to an area of another region among the first region R1, the second region R2, the third region R3, the fourth region R4, the fifth region R5 and the sixth region R6 is set within a range of ±50%. As a result, the area of each of the first region R1 to the sixth region R6 is sufficiently secured. Further, in the first embodiment, the area of each of the third region R3, the fourth region R4, the fifth region R5, and the sixth region R6 is set to 0.6 mm² or more, so that each area is sufficiently secured. Thus, even when the pupil is smaller than the outer region RO, an appropriate field of vision corresponding to the range of the refractive power between the reference refractive power and the strong refractive power is easily obtained.

As shown in FIG. 3, in the transition region (in the first embodiment, the second region R2, the fourth region R4 and the sixth region R6), the refractive power is increased or decreased to be proportional to the distance from the axis O. Thus, a possibility can be reduced that the refractive power largely out of the desired refractive power is caused in a portion of the transition region, compared to a configuration in which the refractive power is not proportional to the distance from the axis O. Accordingly, the lens part is easily designed. Further, the area of each of the second region R2, the fourth region R4 and the sixth region R6 is equal to or larger than the area of the first region R1 (in this embodiment, the areas of the first region R1 to the sixth region R6 are identical to each other). As a result, the field of vision corresponding to the refractive power between the reference refractive power and the strong refractive power is further appropriately obtained.

(Countermeasure to Change of Size of Pupil)

As shown in FIG. 3, the refractive power in the second region R2 is changed as the distance from the axis O becomes larger, to be opposite to the change of the refractive power in the fourth region R4. Further, the first region R1, the second region R2, the third region R3, and at least a part of the fourth region R4 (in this embodiment, the whole part of the fourth region R4) are arranged within a region having a radius of 1.5 mm corresponding to a radius of the pupil of a human being that has been contracted to some extent. Thus, even when the pupil of a wearer is contracted to some extent, the light to the retina passes through the first region R1 to which the first refractive power is added, the third region R3 to which the third refractive power is added, and the transition region (the second region R2 and the fourth region R4) in which the refractive power varies between the first refractive power and the third refractive power. Accordingly, an appropriate field of vision corresponding to the range of the refractive power between the first refractive power and the third refractive power can be easily obtained regardless of the change of the size of the pupil of a wearer.

Specifically, in the first embodiment, the first refractive power that is added to the first region R1 is the strong refractive power, and the third refractive power that is added to the third region R3 is the reference refractive power. As described above, the strong refractive power stronger than the reference refractive power is added to the first region R1 in which the aberration is hardly caused, so that the influence to the field of vision of a wearer caused by the aberration or the like is decreased, compared to a configuration in which the reference refractive power is added to the first region R1.

As shown in FIG. 2 and FIG. 3, in the first embodiment, the first region R1, the second region R2, and a part of the third region R3 are arranged within a region having a radius of 1.0 mm around the axis O of the lens part 2. In a light environment, the pupil of a human being is contracted to a radius of approximately 1.0 mm or less. In a case in which the first region R1, the second region R2, and at least a part of the third region R3 are arranged within a region having a radius of 1.0 mm around the axis O, the light to the retina passes through each of the first region R1, the second region R2, and the third region R3 even in an extremely light environment. Thus, even when the pupil of a wearer is contracted to be extremely small, an appropriate field of vision corresponding to the range of the refractive power between the reference refractive power and the strong refractive power can be easily obtained.

As described above, in the first embodiment, the two strong refractive power regions and the reference refractive power region between the two strong refractive power regions are arranged inside the ring-like outer region RO. That is, the first region R1, the second region R2, the third region R3, the fourth region R4, the fifth region R5, and at least a part of the sixth region R6 are arranged within a region having a radius of 1.5 mm around the axis O of the lens part 2. Thus, even when the pupil of a wearer is contracted to some extent, the light to the retina easily and appropriately passes through each of the two strong refractive power regions, the reference refractive power region, and the transition region. Accordingly, an appropriate field of vision corresponding to the range of the refractive power between the reference refractive power and the strong refractive power can be easily obtained regardless of the change of the size of the pupil of a wearer.

A configuration of each of the third region R3 to the sixth region R6 may be changed. For example, similar to the outer region RO, the reference refractive power may be added to each of the third region R3 to the sixth region R6. Also in this case, the superior field of vision in which the loss of light is decreased can be obtained by the first region R1 and the second region R2. Further, the fifth region R5 between the fourth region R4 and the sixth region R6 may be omitted. Also in this case, the field of vision corresponding to the range of the refractive power between the reference refractive power and the strong refractive power can be obtained.

Second Embodiment

An intraocular lens of the second embodiment is now described with reference to FIG. 6. In the intraocular lens of the second embodiment, the arrangements of the regions in the lens part 2 and the refractive power in each region are different from those of the intraocular lens 1 of the first embodiment, while other configuration is identical to that of the intraocular lens 1 of the first embodiment. Thus, the configuration of the intraocular lens of the second embodiment identical to that of the intraocular lens 1 of the first embodiment is described briefly or the description thereof is omitted. Similar to the first embodiment, the intraocular lens of the second embodiment fulfills requirement for intraocular lenses that collects much incident light that is incident on the lens part 2, in the vicinity of a specified focal point (in this embodiment, a single focal point). The requirement for intraocular lenses is that the MTF curve at spatial frequency of 50 lp/mm has one maximal value and no minimal value in a range of a defocusing value of −0.5 D to 0.5 D.

(Regions in Lens Part)

The regions in the lens part 2 of the intraocular lens of the second embodiment are now described. As shown in FIG. 6, the regions R1 to R4 and RO are disposed concentrically in the lens part 2 around the axis O.

The first region R1 is a circular region located at the centermost position among a plurality of the regions. Each of the second region R2, the third region R3, the fourth region R4, and the outer region RO is a ring-like region. The second region R2 is located adjacent to the first region R1 at an outer side of the first region R1. The third region R3 is located adjacent to the second region R2 at an outer side of the second region R2. The fourth region R4 is located adjacent to the third region R3 at an outer side of the third region R3. The outer region RO is located adjacent to the fourth region R4 at an outer side of the fourth region R4.

(Refractive Power in Each Region)

The refractive power in each of the regions R1 to R4 and RO in the lens part 2 of the second embodiment is now described. In the graph shown in FIG. 6, similar to the graph shown in FIG. 3, a horizontal axis denotes a distance from the axis O in the lens part 2, and a vertical axis denotes the refractive power (diopter) of the lens part 2.

The refractive power (first refractive power) of the first region R1 is the reference refractive power (0 (D) in this embodiment). Specifically, the first region R1 in this embodiment is formed to uniformly have the reference refractive power of 0 (D) regardless of the distance from the axis O.

In the second region R2, the refractive power is increased from the first refractive power, as the distance from the axis O becomes larger. Specifically, the refractive power in the second region R2 is increased from the reference refractive power in the first region R1 to a third refractive power (the strong refractive power) added to the third region R3, as the distance from the axis O becomes larger. The refractive power in the second region R2 of this embodiment is increased to be proportional to the distance from the axis O.

The refractive power (the third refractive power) added to the third region R3 is the strong refractive power stronger than the reference refractive power. Specifically, the strong refractive power is uniformly added to the third region R3 of this embodiment regardless of the distance from the axis O.

In the fourth region R4, the refractive power is decreased from the third refractive power, as the distance from the axis O becomes larger. Specifically, the refractive power in the fourth region R4 is decreased from the strong refractive power in the third region R3 to the reference refractive power added to the outer region RO, as the distance from the axis O becomes larger. The fourth region R4 of this embodiment includes a region (hereinafter, also referred to as a "constant region") in which the refractive power is constant regardless of the distance from the axis O. However, the fourth region R4 need not necessarily include the constant region. The refractive power in a region other than the constant region among the fourth region R4 of the second embodiment is decreased to be proportional to the distance from the axis O.

The refractive power added to the outer region RO is the reference refractive power. Specifically, the reference refractive power is uniformly added to the outer region RO of this embodiment regardless of the distance from the axis O. However, the reference refractive power added to the outer region RO may vary within the outer region RO in order for correction of the aberration. In this embodiment, the reference refractive power added to the first region R1 is identical to the reference refractive power added to the outer region RO. However, the reference refractive power added to the first region R1 need not necessarily be strictly identical to the reference refractive power added to the outer region RO. For example, a change rate of the reference refractive power in the first region R1 relative to the reference refractive power in the outer region RO may be set within a range of ±30% (preferably ±20%). Also in this case, an appropriate field of vision can be obtained regardless of the change of the size of the pupil of a wearer.

(Area of Each Region)

In this embodiment, a change rate of an area of any region relative to an area of another region among the first region R1, the second region R2 and the third region R3 is set within a range of ±50%. Specifically, in this embodiment, the lens part 2 is designed such that the areas of the first region R1 to the third region R3 are identical to each other.

Further, in this embodiment, the area of each of the first region R1, the second region R2, the third region R3 and the fourth region R4 is set to 0.6 mm$^2$ or more. Specifically, in this embodiment, the area of each of the first region R1 to the fourth region R4 is set to 1.1 mm$^2$ or more.

(Decreasing of Loss of Light)

Figure 6:
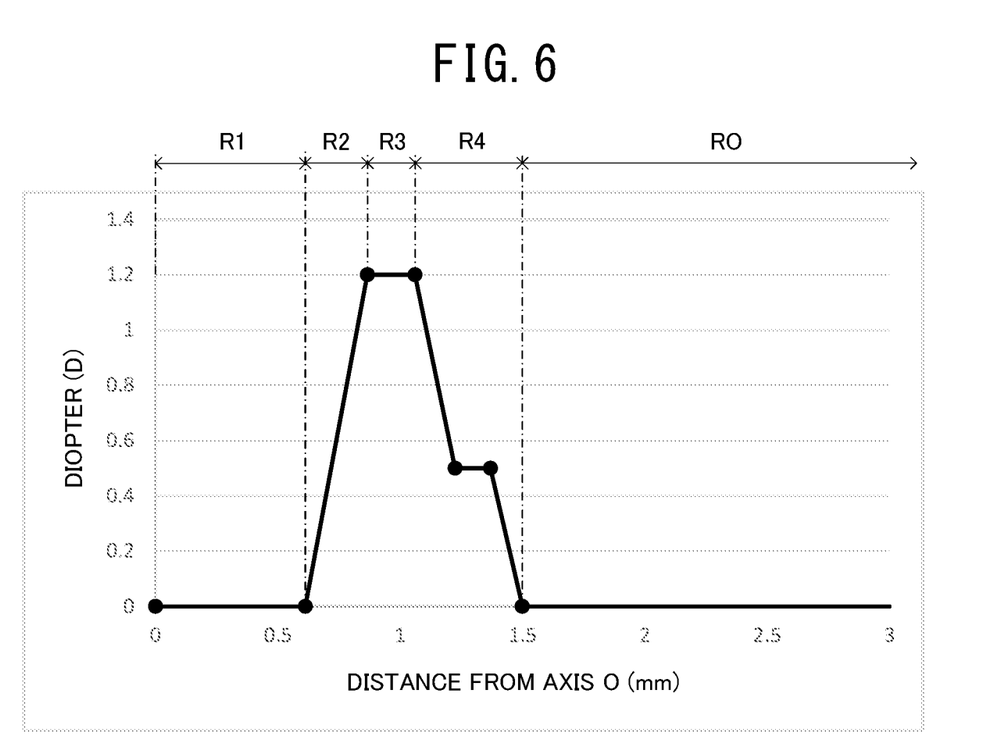
FIG. 6 is a graph illustrating a relation between a distance from an axis O of a lens part 2 of the second embodiment and a refractive power (diopter) of the lens part 2.

As shown in FIG. 6, the first refractive power (in the second embodiment, the reference refractive power) is uniformly added to the first region R1 regardless of the distance from the axis O. Accordingly, a wearer can appropriately recognize a field of vision corresponding to the first refractive power (namely, the field of vision obtained by the light passing through the first region R1), compared to a configuration in which the refractive power is decreased or increased at a position slightly apart from the axis O. Thus, an amount of light that is not recognized by a wearer is decreased, so that a superior field of vision can be easily obtained. Further, the wearer can also obtain the field of vision corresponding to the range of the refractive power closer to the first refractive power, using the light passing through the second region R2. Consequently, according to the technique of this disclosure, the depth of focus can be appropriately expanded while decreasing an amount of the light that is not recognized by a wearer, among the light passing through the lens part 2.

A change rate of the area of the second region R2 relative to the area of the first region R1 is within a range of ±50%. As a result, the area of each of the first region R1 and the second region R2 is sufficiently secured. In the second embodiment, the area of each of the first region R1 and the second region R2 is set to 0.6 mm$^2$ or more, so that the area of each of the first region R1 and the second region R2 is sufficiently secured. Thus, both of the field of vision corresponding to the first refractive power and the field of vision corresponding to the range of the refractive power closer to the first refractive power are further appropriately and easily obtained.

The area of the each of the second region R2 and the fourth region R4 is equal to or larger than the area of the first region R1. As a result, the area of each of the second region R2 and the fourth region R4 in which the refractive power varies in response to the distance from the axis O is appropriately secured. Thus, the field of vision corresponding to the range of the refractive power closer to the first refractive power is appropriately obtained. That is, the depth of focus of the intraocular lens 1 is further appropriately expanded.

In the second embodiment, the area of each of the third region R3 and the fourth region R4 is also set to 0.6 mm$^2$ or more, so that the area of each of the third region R3 and the fourth region R4 is sufficiently secured. Thus, even when the pupil is smaller than the outer region RO, an appropriate field of vision corresponding to the range of the refractive power between the reference refractive power and the strong refractive power is easily obtained.

(Countermeasure to Change of Size of Pupil)

The refractive power in the second region R2 is changed as the distance from the axis O becomes larger, to be opposite to the change of the refractive power in the fourth region R4. Further, the first region R1, the second region R2, the third region R3, and at least a part of the fourth region R4 are arranged within a region having a radius of 1.5 mm corresponding to a radius of the pupil of a human being that has been contracted to some extent. Thus, even when the pupil of a wearer is contracted to some extent, the light to the retina passes through the first region R1 to which the first refractive power is added, the third region R3 to which the third refractive power is added, and the transition region (the second region R2 and the fourth region R4) in which the refractive power varies between the first refractive power and the third refractive power. Accordingly, an appropriate field of vision corresponding to the range of the refractive power between the first refractive power and the third refractive power can be easily obtained regardless of the change of the size of the pupil of a wearer.

Specifically, in the second embodiment, the first refractive power that is added to the first region R1 is the reference refractive power, and the third refractive power that is added to the third region R3 is the strong refractive power. In this case, the number of the regions arranged inside the outer region RO is four which is as small as possible. As the number of the regions becomes smaller, an amount of the aberration is easily suppressed. Thus, by setting the number of the regions arranged inside the outer region RO to four, an appropriate field of vision can be easily obtained regardless of the size of the pupil of a wearer while restricting the aberration from causing.

In the second embodiment, the first region R1, the second region R2, and a part of the third region R3 are arranged within a region having a radius of 1.0 mm around the axis O of the lens part 2. As described above, in a light environment, the pupil of a human being is contracted to a radius of approximately 1.0 mm or less. In a case in which the first region R1, the second region R2, and at least a part of the third region R3 are arranged within a region having a radius of 1.0 mm around the axis O, the light to the retina passes through each of the first region R1, the second region R2, and the third region R3 even in an extremely light environment. Thus, even when the pupil of a wearer is contracted to be extremely small, an appropriate field of vision corresponding to the range of the refractive power between the reference refractive power and the strong refractive power can be easily obtained.

The techniques disclosed in the above-described embodiments are merely examples. Thus, the techniques exemplarily described in the above-described embodiments may be modified. For example, a part of the techniques in the first embodiment or the second embodiment may be applied to an intraocular lens.

What is claimed is:

1. An intraocular lens comprising a lens part, wherein:
   the lens part includes regions each having a circular or ring shape, the regions being disposed concentrically around an axis of the lens part,
   the regions in the lens part include:
      a first region that is a circular region located at the centermost position, a first refractive power being uniform in the first region regardless of the distance from the axis,
      a second region that is a ring-shape region located adjacent to the first region at an outer side of the first region, the second region having a refractive power that is increased or decreased from the first refractive power as the distance from the axis becomes larger, and
      an outer region that is a ring-shape region located at an outer side of the second region, the outer region having a reference refractive power for focusing on a far point,
      an MTF curve at spatial frequency of 50 lp/mm relating to light passing through a region having a radius of 1.5 mm around the axis of the lens part has one maximal value and no minimal value in a range of a defocusing value of −0.5 D to 0.5 D, and
      a change rate of an area of the second region relative to an area of the first region is within a range of ±50%.

2. The intraocular lens as defined in claim 1, wherein an area of each of the first region and the second region is 0.6 mm$^2$ or more.

3. The intraocular lens as defined in claim 1, wherein:
   the first refractive power of the first region is a strong refractive power stronger than the reference refractive power, and
   the refractive power of the second region is decreased from the strong refractive power in the first region as the distance from the axis becomes larger.

4. The intraocular lens as defined in claim 3, wherein:
   the regions in the lens part further include:
      a third region that is a ring-shape region located adjacent to the second region at an outer side of the second region, the third region being configured to have the reference refractive power,
      a fourth region that is a ring-shape region located adjacent to the third region at an outer side of the third region,
      a fifth region that is a ring-shape region located adjacent to the fourth region at an outer side of the fourth region, the fifth region having the strong refractive power, and
      a sixth region that is a ring-shape region located adjacent to the fifth region at an outer side of the fifth region and located adjacent to the outer region at an inner side of the outer region,
   in the fourth region, the refractive power is increased from the reference refractive power in the third region to the strong refractive power in the fifth region as the distance from the axis becomes larger, and
   in the sixth region, the refractive power is decreased from the strong refractive power in the fifth region to the reference refractive power in the outer region as the distance from the axis becomes larger.

5. The intraocular lens as defined in claim 4, wherein a change rate of an area of any region relative to an area of another region among the first region, the second region, the third region, the fourth region, the fifth region and the sixth region is within a range of ±50%.

6. The intraocular lens as defined in claim 4, wherein the area of each of the first region, the second region, the third region, the fourth region, the fifth region and the sixth region is set to 0.6 mm$^2$ or more.

7. The intraocular lens as defined in claim 4, wherein the first region, the second region, the third region and at least a part of the fourth region are arranged within a region having a radius of 1.5 mm around the axis of the lens part.

8. The intraocular lens as defined in claim 7, wherein the first region, the second region and at least a part of the third region are arranged within a region having a radius of 1.0 mm around the axis of the lens part.

9. The intraocular lens as defined in claim 4, wherein the first region, the second region, the third region, the fourth region, the fifth region and at least a part of the sixth region are arranged within a region having a radius of 1.5 mm around the axis of the lens part.

10. The intraocular lens as defined in claim 1, wherein:
    the regions in the lens part further include:
       a third region that is a ring-like region located adjacent to the second region at an outer side of the second region, the third region having a third refractive power different from the first refractive power being, and a fourth region that is a ring-like region located adjacent to the third region at an outer side of the third region, the first refractive power of the first region is the reference refractive power, the third refractive power of the third region is a strong refractive power stronger than the reference refractive power, in the second region, the refractive power is increased from the reference refractive power in the first region to the strong refractive power in the third region as the distance from the axis becomes larger, the outer region is located adjacent to the fourth region at an outer side of the fourth region, and in the fourth region, the refractive power is decreased from the strong refractive power in the third region to the reference refractive power in the outer region as the distance from the axis becomes larger.

11. The intraocular lens as defined in claim 10, wherein the first region, the second region and at least a part of the third region are arranged within a region having a radius of 1.0 mm around the axis of the lens part.

* * * * *